United States Patent [19]

Einzig et al.

[11] Patent Number: 5,030,637

[45] Date of Patent: Jul. 9, 1991

[54] ANISODAMINE TO PREVENT AND TREAT EYE DISEASE

[75] Inventors: Stanley Einzig, Golden Valley, Minn.; Shu-Lun Zhang, Beijing, China

[73] Assignee: Regents of the University of Minnesota, Minneapolis, Minn.

[21] Appl. No.: 579,474

[22] Filed: Sep. 10, 1990

Related U.S. Application Data

[60] Division of Ser. No. 296,712, Jan. 17, 1989, Pat. No. 4,971,976, which is a continuation-in-part of Ser. No. 153,238, Feb. 8, 1988, abandoned.

[51] Int. Cl.$^5$ ............................................. A61K 31/44
[52] U.S. Cl. ..................................... 514/304; 514/912
[58] Field of Search ................................. 514/304, 912

[56] References Cited

PUBLICATIONS

Chem. Abst., 110:226915d, (1989), Li et al.
S. Zhang et al., Pediatric Res. 20,177a, (1986).
Pharmacologic Effects of Anisodamine, Chines Med. J., 7, 133–138, (1975).
Fed. Proc., vol. 23, 4, Part 2, May 1988, p. 882.

*Primary Examiner*—Stanley J. Friedman
*Assistant Examiner*—Zohyeh A. Fay
*Attorney, Agent, or Firm*—Merchant, Gould, Smith, Edell, Welter & Schmidt

[57] ABSTRACT

A method is disclosed for the prevention and alleviation of pathologic changes in the eye such as diabetic retinopathy or senile macular degeneration. The claimed method involves the parenteral administration of anisodamine in an amount effective for preventing or alleviating these pathogenic changes.

5 Claims, 3 Drawing Sheets

ANISODAMINE TO PREVENT AND TREAT EYE DISEASE

CROSS-REFERENCE TO RELATED APPLICATION

This is a division of application Ser. No. 07/296,712, filed Jan. 17, 1989, now U.S. Pat. No. 4,971,976.

This application is a continuation-in-part of U.S. application Ser. No. 153,238, filed Feb. 8, 1988 now abandoned.

FIELD OF THE INVENTION

This invention relates to a new therapeutic use for anisodamine. More particularly, the present invention concerns the use of anisodamine to prevent and treat pathologic changes of the eye such as senile macular degeneration and diabetic retinopathy.

BACKGROUND OF THE INVENTION

As one of the most serious complications of diabetes mellitus, diabetic retinopathy is a major cause of blindness all over the world. In fact, diabetic retinopathy occurs in about 4.4 million of the estimated 11 million persons with diabetes in the United States. Every year approximately 4,700 of these patients become blind. In light of current prolonged survival rates for diabetic patients coupled with an increased likelihood of retinopathy in long term diabetics, the incidence of retinopathy can only be expected to increase in the future.

In spite of the wide clinical variation of the different stages of diabetic retinopathy, there are generally three processes that are known or thought to be a pathogenetic importance. The first is usually characterized by microangiopathy, ischemia and hypoxia. Visible signs of this process include capillary obliteration or nonperfusion, arteriolar-venular shunt, hyperaggregation of red cells and platelets, sluggish blood flow and an impaired ability of red cells to release oxygen. The second process involves abnormal metabolism of carbohydrate, protein and arachidonic acid.

The third process of diabetic retinopathy is thought to involve lipid peroxidation of the retinal membrane, possibly oxygen radical-induced. Studies have shown that the lipid peroxidation product (malondialdehyde) level in a diabetic patient's blood plasma is significantly higher than that of normal subjects. H. Kaji et al., "Increased Lipoperoxide Value and Gutathione Peroxidase Activity of Type 2 (Non-Insulin Dependent) Diabetic Women," *Klin. Wochenschr.*, 63, 765–768 (1985). Moreover, it has been found that the retina is particularly susceptible to damage by oxygen. C. H. Chen and A. Patz, "Component of Vitreous-Soluble Protein, Effect of Hyperoxia and Age," *Invest. Opthalmal.*, 15, 228–232 (1976). Lipid peroxidation of the retinal membrane may also be caused by exposure to ultraviolet radiation. H. Pasantes-Morales and C. Cruz, "Taurine and Hyptaurine Inhibit Light-Induced Lipid Peroxidation and Protect Rod Outer Segment Structure," *Brain Res.*, 330, 154–154 (1985). Although many of these characteristics of diabetic retinopathy are known, effective prevention and therapy for this disease is not available.

Senile macular degeneration, associated with aging and drusen, is the leading cause of severe visual loss in the United States and Western Europe in persons aged 55 years or older. It is of unknown cause, and no treatment has been shown to be of benefit to the majority of people who have nonexulative disease. Although drusen are the ophthalmoscopic hallmark of macular degeneration, the primary lesion appears to be in the retinal pigment epithelium (RPE). R. W. Young, *Surv. Ophthalmol.*, 31, 291 (1987) relates macular degeneration to the gradual accumulation of lipofuscin in RPE cells, which is in turn thought to be related to photoxidative damage mechanisms. Therefore, the RPE may have a particular vulnerability to lipofuscin accumulation because of the normal daily phagucytic load of membranes rich in polyunsaturated acids, combined with the high-oxygen environment and the lifelong potential for light-induced free radical damage in the cells. See J. J. Weiter, *Arch. Ophthalmol.*, 106, 183 (1988).

Anisodamine (6(s)-hydroxyhyoscyamine) is an alkaloid isolated from *Anisodus tanguticus* (solanaceae), a Chinese herb plant. Its chemical structure is only slightly different from that of atropine in that it possesses an hydroxy group on the sixth position of the tropane radical as shown in formula I:

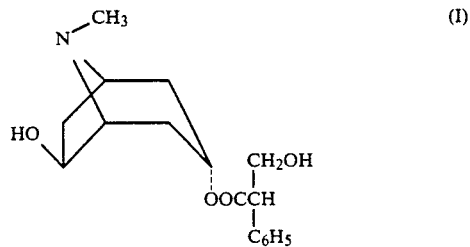

In numerous medical studies, anisodamine has been identified as an anticholingeric agent and a vasodilator, with a weaker, and less toxic, effect than atropine.

In view of its ability to enhance microcirculation, anisodamine has been used in China since 1965 for treating many diseases including septic shock, severe lobar pneumonia, pancreatitis, central serous retinochoroiditis and myopia. See generally C. P. Li, *Chinese Herbal Medicine*. A publication of the John E. Fogarty International Center for Advanced Study in the Health Sciences, U.S. Department of Health, Education and Welfare, Public Health Service, NIH, DHEW Publication No. 75-732 pp. 11–20 (1974); "Anisodamine in the Treatment of Some Diseases with Manifestations of Acute Microcirculatory Insufficiency," *Chinese Medical Journal*, 1, 127–132 (March 1975). However, a further need exists for the development of new anisodamine-based treatments.

SUMMARY OF THE INVENTION

The present invention provides a therapeutic method comprising administering anisodamine or a pharmaceutically-acceptable salt thereof to a human, or other mammal, in an amount effective to prevent or alleviate diabetic retinopathy or senile macular degeneration.

The present method is based upon our discovery that anisodamine selectively increases blood flow and oxygen delivery to the retina-choroid and iris ciliary body of the eye. Anisodamine also significantly protects isolated retina cells against lipid peroxidation induced by ultraviolet radiation, alloxan and arachidonic acid. Furthermore, anisodamine protects isolated pancreatic $\beta$ cells against alloxan-induced lipid peroxidation and enhances insulin secretion from such cells.

While retinopathy is a consequence of diabetes mellitus, the treatment of the present invention is not limited to diabetic patients. Rather, anisodamine can be used to treat or prevent pathologic changes in the eye, such as senile macular degeneration, which are associated with exposure to ultraviolet radiation, ischemia, hypoxia and lipid peroxidation of retinal cells.

The method of the present invention includes the systemic and topical administration of an effective amount of anisodamine to an individual likely to develop, or suffering from, symptoms and pathologic changes associated with retinopathy or senile macular degeneration. The method of administration includes oral and parenteral means, including intravenous injection or infusion, and eyedrops. Anisodamine is preferably combined with a pharmaceutically-acceptable carrier for the desired mode of administration.

DETAILED DESCRIPTION OF THE INVENTION

Figure 1:
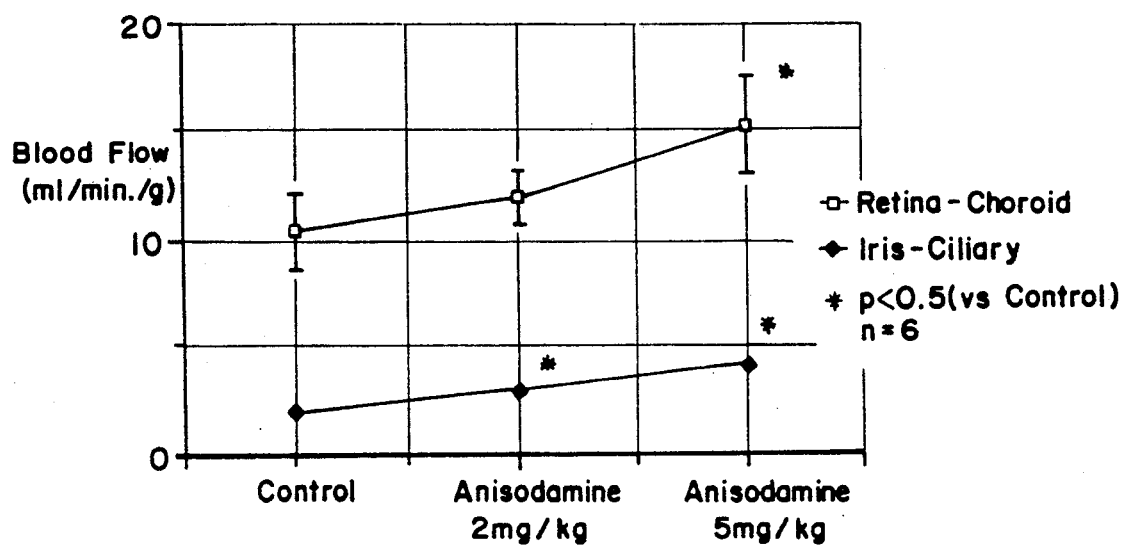
FIG. 1 is a graphic depiction summarizing the effect of anisodamine on blood flow to the retina-choroid and iris ciliary body.

The structure of anisodamine (6(s)-hydroxyhyoscyamine) is depicted in formula I, hereinabove. Anisodamine is an alkaloid which can be isolated from *Anisodus tanguticus* (solanaceae). In benzene, it forms color-less needle-shaped crystals, melting at about 62°–64° C.

Methods for the synthesis of anisodamine, its acid addition salts and the corresponding N-oxide have been published. For example, see J.-X. Xie et al., *Chem. Nat. Prod. Proc. Sino Am. Symp.*, 131 (1982); J.-X. Xie et al., *Yaoxue Xuebao*, 16, 762 (1981) [*Chem. Abstr.*, 96, 162990g (1982)]; J.-X. Xie et al., *Yaoxue Xuebao*, 16, 767 (1981) [*Chem. Abstr.*, 96, 143127q (1982)]; J.-X. Xie, *Yao Hsueh Pao*, 15, 403 (1980) [*Chem. Abstr.*, 94, 121757b (1981)].

The use of pharmaceutically-acceptable salts of anisodamine is also within the scope of the present invention. Pharmaceutically-acceptable amine salts may be salts of organic acids, such as acetic, mucic, lactic, malic, or p-toluene sulphonic acid, and the like as well as salts of pharmaceutically-acceptable mineral acids, such as phosphoric, nitric hydrochloric or sulfuric acid, and the like. The hydrobromide salt is white needle-like crystals which are readily soluble in water, m.p. 162°–163° C., $[\alpha]_D^{18}$–10.4($H_2O$, C 2.24). Furthermore, ($C_1$–$C_5$)alkyl halides or ($C_1$–$C_5$)dialkyl sulfates may be used to quaternize the tertiary nitrogen atom of anisodamine, thereby forming the corresponding alkyl halide salt, or alkyl sulfate salt, e.g., the methyl bromide, methyl sulfate and the like. Also, useful anisodamine analogs may be prepared by oxidizing the tertiary nitrogen atom of anisodamine to the corresponding N-oxide, e.g., with hydrogen peroxide. For example, see Polonovski, *Bull. Soc. Chim. France*, 39, 1147 (1926). Anisodamine and its salts may exist in the form of optical isomers, and these isomers, as well as racemic ($\pm$) mixtures are included within the scope of this invention.

Pharmaceutical compositions comprising anisodamine or a salt thereof in combination with a pharmaceutically-acceptable carrier may be prepared from standard ingredients using standard techniques. For example, topical compositions such as eyedrops include standard liquid formulations, e.g., distilled water or physiological saline solutions, in combination with non-toxic thickeners and preservatives. Creams and ointments, e.g., oil-in-water or water-in-oil emulsions, and other physiologically-acceptable carriers such as gelatin, vegetable oils, polyalkylene glycol or alcohol may also be used. Injectable formulations use aqueous physiologically-acceptable carriers, e.g., distilled water, and preferably contain a compatible buffer system selected to maintain the pH in the desired range of 6.5 to 8, preferably about 7.0 to 7.4. A typical buffer system is a combination of sodium dibasic phosphate and sodium monobasic phosphate.

Oral compositions include tablets, capsules, syrups, elixirs and suspensions. The typical acceptable pharmaceutical carriers for use in the oral formulations described above are exemplified by sugars as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate, calcium sulfate; polyvinyl pyrrolidone, polyvinyl alcohol, stearic acid, alkaline earth metal stearates such as magnesium stearate and calcium stearate; vegetable oils such as peanut oil, cottonseed oil, sesame oil, olive oil and corn oil; nonionic, cationic and anionic surfactants; ethylene glycol polymers; beta-cyclodextrin; fatty alcohols and hydrolyzed cereal solids; as well as other non-toxic compatible filters, binders, disintegrants, buffers, antioxidants, lubricants, flavoring agents, and the like commonly used in pharmaceutical formulations.

Compositions of this invention may be administered one or more times daily. For human dosage, effective amounts of anisodamine would fall generally in the range of 60 mg to about 100 mg per day, either orally or intravenously, e.g., about 0.5 mg to 2 mg per kg body weight per day. In Y. Z. Zhou, *Investigation of the Effectiveness of Henbane Drug for Treating Diabetes*, supra, this amount was found to be beneficial for reducing hyperglycemia. Daily doses as high as about 50 mg/kg, preferably about 10 mg/kg per day give useful therapeutic responses. Eyedrops and other topical preparations may contain at least about 0.1-2% by weight of the active ingredient.

From the following examples, the inventors conclude that anisodamine can be used in effective amounts to act as a prophylactic and as a combatant against many of the pathologic changes associated with retinopathy or macular degeneration. While the precise mechanism and pathogenesis of retinopathy is yet to be elucidated, retinopathy is associated with both diabetes mellitus and lipid peroxidation of retinal cells. As noted above, senile macular degeneration has also been associated with photo-oxidative damage mechanisms. Studies have revealed that lipid peroxidation can be induced by ultraviolet radiation, alloxan (a diabetogenic drug), and arachidonic acid.

With several of the known characteristics of these pathologies in hand, we examined the pharmacological effects of anisodamine. As the following examples demonstrate, anisodamine possesses unique properties that render it a useful compound for both study of the pathogenesis of retinopathy and for the relief from certain pathologic changes associated with the onset and progression of retinopathy or macular degeneration.

In the following examples, a pharmaceutical grade of anisodamine was obtained from Beijing Drug Factory, Beijing, China. The compound was dissolved in distilled water and adjusted to pH 7.4 with HCl. Sodium arachidonate was purchased from NU Chek Prep, Inc., in Elysian, Minn. Alloxan monohydrate, tetramethoxypropane and all other reagents were purchased from Sigma Co. of St. Louis, Mo.

EXAMPLE A

Enhanced Regional Bloodflow and Oxygen Delivery

Experiments were carried out on awake lambs 2.5 to 3 weeks old weighting generally between 6 to 9 kilograms. Five to seven days prior to the experiment, the lambs were placed under sodium pentothol and halothane general anesthesia. An 8 F umbilical catheter was implanted into the lamb via the left atrial appendage into the body of the left atrium. The ductus arteriosus was then ligated.

On the day of the experiment, the lambs were anesthetized with 10 mg/kg i.m. of ketamine HCl and a subcutaneous 2% lidocaine infiltration. Catheters were positioned in the right atrium, the pulmonary artery and the aorta. The lambs were allowed to stabilize for one hour after catheter placement. Following this stabilization period, hemodynamic, regional blood flow and blood gases were measured consecutively at four time points separated by 10-minute intervals. Over these time intervals, the lambs were given control 1, control 2, anisodamine 2 mg/kg and anisodamine 5 mg/kg. Anisodamine was at a concentration of 10 mg/ml and was given as a bolus via the right atrial catheter. Each animal served as its own control.

Intravascular pressures were monitored with Statham P23Db pressure transducers and recorded on the Electronics for Medicine DR12 recorder. Regional blood flow was measured with 15±5 μm radiolabeled microspheres according to the techniques used in S. Einzig et al., "Acute Effects of Amrinone on Regional Myocardial and Systemic Blood Flow Distribution in the Dog," *Can. J. Physiol. Pharmacol.*, 60, 811-818 (1982). The microspheres were injected through the left atrial catheter while the reference blood samples were withdrawn from the aorta at a rate of 3.5 ml/min. for a period of two minutes. At the end of the experiment, the animals were sacrificed by an overdose of pentobarbital. Tissue samples were taken from 100 different locations on each animal and blood flow was determined using standard techniques as discussed in S. Einzig, *Acute Effects of Amrinone, supra*. Blood oxygen contents were measured with a Lex-02-Con machine available from Lexington Instruments. Blood gases were determined with a blood gas meter.

Figure 2:
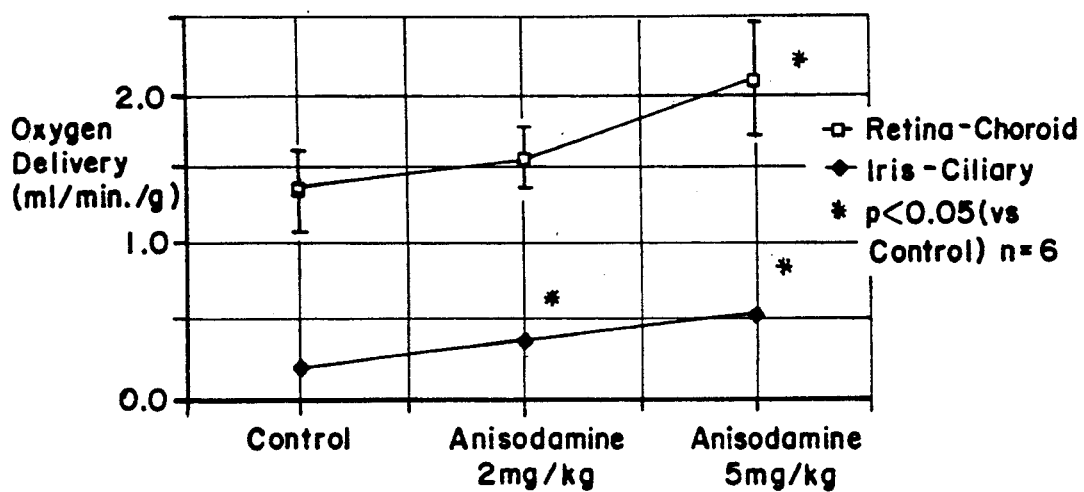
FIG. 2 is a graphic depiction summarizing the effect of anisodamine on oxygen-delivery to the retina-choroid and iris ciliary body.

Of the 100 tissue samples examined on each animal, blood flow and oxygen delivery was most consistently increased in only one regional vascular bed. Surprisingly, we found that anisodamine selectively increased blood flow and oxygen delivery only to the retina-choroid and iris ciliary body of the eye. This increase ranged from 50 to 100 percent and was generally dose dependent. FIGS. 1 and 2 summarize the enhancing effect of anisodamine on blood flow to the retina-choroid and iris ciliary body and the effect of anisodamine on oxygen delivery to the retina-choroid and iris ciliary body.

Figure 3:
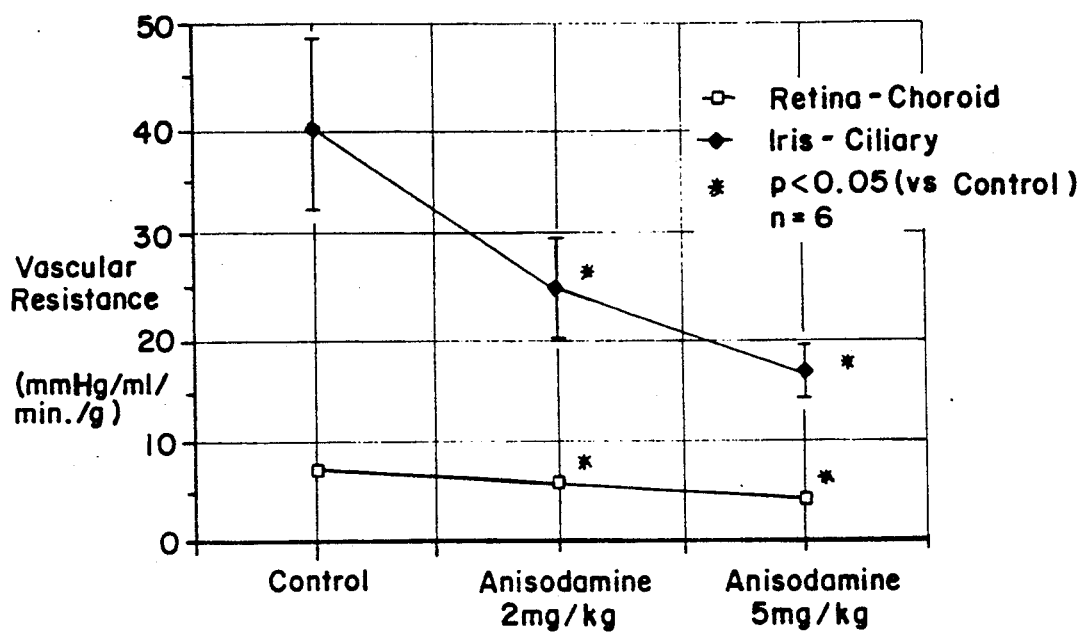
FIG. 3 is a graphic depiction summarizing the effect of anisodamine on the vascular resistance of the retinal blood vessels.

The corresponding vascular resistances were also found to be significantly decreased as shown in FIG. 3. These results demonstrate that anisodamine has a highly selective vasodilatory effect on the retinal blood vessels. Due to the compound's ability to selectively increase blood flow and oxygen delivery to the retinal cells, it is reasonable to conclude that anisodamine would be an effective tool against certain pathologic changes in the eye associated with diabetic retinopathy. Pathologic changes in the eye associated with diabetic retinopathy include microangiography, sluggish blood flow and hyperaggregation of red cells and platelets. Increased blood flow and oxygen levels to the retinal cells would counteract such pathologic changes in the eye.

Indeed, anisodamine is known to inhibit thomboxane synthesis, granulocyte aggregation and platelet aggregation, further characteristics of diabetic retinopathy. Xiu, R-J et al., "Anisodamine inhibits Thromboxane Synthesis, Granulocyte Aggregation and Platelet Aggregation," *JAMA*, 247, 1458-1460 (1982). Considering our new discoveries coupled with the known pharmacological properties of anisodamine, it is reasonable to conclude that anisodamine can effectively combat pathologic changes associated with retinopathy.

EXAMPLE B

Lipid Peroxidation of In Vitro Retinal Cells

1. Ultraviolet radiation-induced lipid peroxidation.

Six to eight month old New Zealand white rabbits weighing approximately 2.7 to 3.2 kgs were killed by exsanguination. Retinal rod outer segment suspensions were prepared using the known Pasantes-Morales method. This method is fully discussed in the article by Pasantes-Morales, H. and Cruz, C., "Taurine and Hypotaurine Inhibit Light-Induced Lipid Peroxidation and Protect Rod Outer Segment Structure," *Brain Res.*, 330, 154-157 (1985). Both eyes were enucleated and appendant tissues were thoroughly removed and rinsed with DPBS having a pH of 7.4. The retinas were then excised. Retinal outer rod segments were separated from the retinas by gently shaking the retinas in a vortex for one minute. The segments were then concentrated by centrifugation at 1,000 g for 15 minutes. The concentration of the retinal rod outer segment suspension was expressed in terms of protein content as measured by Lowry's method. Lowry's method is fully discussed in O. H. Lowry et al., "Protein Measurement with the Folin Phenol Reagent," *J. Biol. Chem.*, 193, 265-275 (1951).

To investigate the lipid peroxidation of retinal rod outer segments (ROS) induced by ultraviolet radiation and the corresponding amount of protection against lipid peroxidation by anisodamine, 0.75 ml of retinal outer rod segment suspension and 0.25 ml of anisodamine (cocentration 10 mg/ml) were mixed and exposed to ultraviolet light at room temperature for two hours. Control samples, each consisting of 0.75 ml of the retinal suspension and 0.25 ml of normal saline, were maintained in the dark for two hours.

Malondialdehyde (MDA) is commonly used as an index of lipid peroxidation. The presence of malondialdehyde was measured by the thiobarbituric acid-acetic acid buffer method discussed by H. Ohkawa et al., "Assay for Lipid Peroxides in Animal Tissues by Thiolbarbituric Acid Reaction," *Anal. Biochem.*, 95, 351-358 (1979). Briefly, 0.3 ml of the retinal suspension was mixed with sodium dodecyl sulfate, acetate buffer at pH 3.5 and thiobarbituric acid solution. After heating at 95° C. for 80 minutes, the pink segment of the mixture was extracted with an Nbutanol-pyridine mixture. The absorbance of the pink segment was measured at 533 nm on a Beckman spectrophotometer. Tetramethoxypropane was used as an external standard. All results are expressed in terms of nmoles of malondialdehyde per 100 mg of protein.

Ultraviolet radiation (UV) was found to increase malondialdehyde production by the retinal suspension approximately ten times that compared to the retinal suspension which had been maintained in the dark. This information confirms that lipid peroxidation of retinal cells can be induced by ultraviolet radiation. More importantly, the addition of anisodamine was found to significantly attenuate the increase in malondialdehyde production. The results of this experiment are shown in Table 1 below:

TABLE 1

| Effect of UV Radiation on MDA Production of ROS and Anisodamine Protection | | | |
|---|---|---|---|
| | Dark | UV (256 nm) | Anisodamine + UV |
| MDA (mean ± SE) nmol/100 mg protein | 575 ± 122 | 5678 ± 578 | 2607 ± 289 |
| n | 4 | 4 | 4 |
| p | | <0.002 (vs Dark) | <0.006 (vs UV) |

UV: 375 μwatts per cm² at 12 cm distance, 2 hrs., Anisodamine final concentration: 2.5 mg/ml Anisodamine was found to attenuate malondialdehyde production, and consequently lipid peroxidation, by 54%. From these results, it is reasonable to conclude that anisodamine can effectively protect against ultraviolet radiation-induced lipid peroxidation.

2. Alloxan-induced lipid peroxidation

To examine alloxan-induced lipid peroxidation of the retinal cells and the protective pharmacological effects of anisodamine, 0.24 ml of the retinal suspension was incubated with either 0.03 ml of DPBS or anisodamine at 37° C. for 30 minutes, followed by the addition of 0.03 ml fresh alloxan. The final concentration of alloxan in the mixture was 1.5 mg/ml and that of anisodamine was 2 mg/ml. After further incubation for a thirty-minute period, the production of malondialdehyde was measured using the same method outlined above for ultraviolet radiation-induced lipid peroxidation. The results of this experiment are set forth in Table 2 below:

TABLE 2

| Effect of Alloxan on MDA Production of ROS and Anisodamine Protection | | | |
|---|---|---|---|
| | Control | Alloxan | Anisodamine + Alloxan |
| MDA (mean ± SE) | 623 ± 107 | 1431 ± 191 | 1195 ± 145 |
| n | 6 | 6 | 6 |
| p | | <0.005 (vs Control) | <0.005 (vs Alloxan) |

Final concentration: Anisodamine 2 mg/ml, Alloxan 1.5 mg/ml. Incubation at 37° C. for 30 min.

As the results summarized in Table 2 demonstrate, alloxan increased retinal malondialdehyde production by 2.3 times in comparison to the control sample. The presence of anisodamine, however, significantly attenuated the increase in retinal malondaldehyde production, and thus lipid peroxidation of the retinal segment, by 17 percent.

3. Arachidonic acid-induced lipid peroxidation

Finally, we investigated arachidonic acid-induced lipid peroxidation of the retinal suspension and any protection provided by the presence of anisodamine. Sodium arachidonate was freshly prepared with DPBS by ultrasonification. The experimental system consisted of 0.24 ml of the retinal suspension and, 0.03 ml anisodamine or DPBS for the control. To each tube, excluding the control, 0.03 ml of sodium arachidonate was added. The final concentration of sodium arachidonate was 0.25 mg/ml. The final concentration of anisodamine was 0.01 mg/ml. The malondialdehyde concentration was measured after incubation of the tubes at 37° C. for 30 minutes using the technique discussed previously.

The results show that arachidonic acid increaed retinal malondialdehyde generation by 3.5 times. Moreover, the addition of anisodamine, even at this low concentration, significantly protected against the increase in malondialdehyde production. The results are summarized below in Table 3:

TABLE 3

| Effect of Arachidonic Acid on MDA Production of ROS and Anisodamine Protection | | | |
|---|---|---|---|
| | Control | Arachidonic Acid | Anisodamine + Arachidonic acid |
| MDA (mean ± SE) nmol/100 mg protein | 452 ± 130 | 1548 ± 464 | 1025 ± 412 |
| n | 4 | 4 | 4 |
| p | | <0.05 (vs Control) | <0.009 (vs Arachidonic acid) |

Final concentration: Anisodamine, 0.01 mg/ml; Sodium Arachidonate 0.25 mg/ml. Incubation at 37° C. for 30 min.

All of our experiments indicate that anisodamine has the ability to significantly attentuate any increase in lipid peroxidation of retinal outer rod segments induced either by ultraviolet radiation, arachidonic acid and alloxan. This pharmacological activity is important as studies show that the level of lipid peroxidation products in diabetics is higher than that found in nondiabetics, leading many to conclude that lipid peroxidation is associated with the onset of retinopathy. Lipid peroxidation is also believed to be associated with senile macular degeneration. Therefore, it is reasonable to conclude that anisodamine could be used to decrease the extent of lipid peroxidation and consequently, to attenuate retinopathy or senile macular degeneration.

EXAMPLE C

Pancreatic β Cell Insulin Secretion

A clonal cell line of hamster transformed pancreatic islet β cell (HIT) of 72-76 passage was used as described in R. S. Hill and A. E. Boyd, III, "Perfusion of a Clonal Cell Line of Simian Virus 40-Transformed Beta Cells: Insulin Secretory Dynamics in Response to Glucose, 3-Isobutyl-1-Methylxanthine and Potassium," *Diabetes*, 34, 115-120 (1985). The cells were grown in five percent $CO_2$ and air at 37° C. and maintained in RPMH 640 medium containing 10% fetal bovine serum. Before each study was conducted, cells were subcultured for 48 hours by plating cells in culture dishes. On the day of the experiment, the culture dishes were washed and incubated with Krebs Ringer bicarbonate Hepes buffer solution (KRB) at 37° C. for 30 minutes to remove any existing insulin in the medium.

1. Enhanced insulin secretion

Our experiments first set out to characterize the effect of anisodamine on insulin secretion. 0.1 ml of various concentrations of anisodamine or KRB was added to each microdish. After incubating the microdishes for 50 minutes, the supernatants were discarded. The microdishes were rinsed twice with 1.0 ml KRB. Subsequently, 1.0 ml of 1.7 mM glucose was added to each microdish. The microdish was then incubated for 60 minutes. The concentration of insulin in the resulting medium was measured by a radioimmunoassay. This technique is known to those skilled in the art and is discussed fully in C. R. Morgan and A. Lazarow, "Immunoassay of Insulin, Two Antibody System," *Diabetes*, 12, 115-126 (1963).

Figure 4:
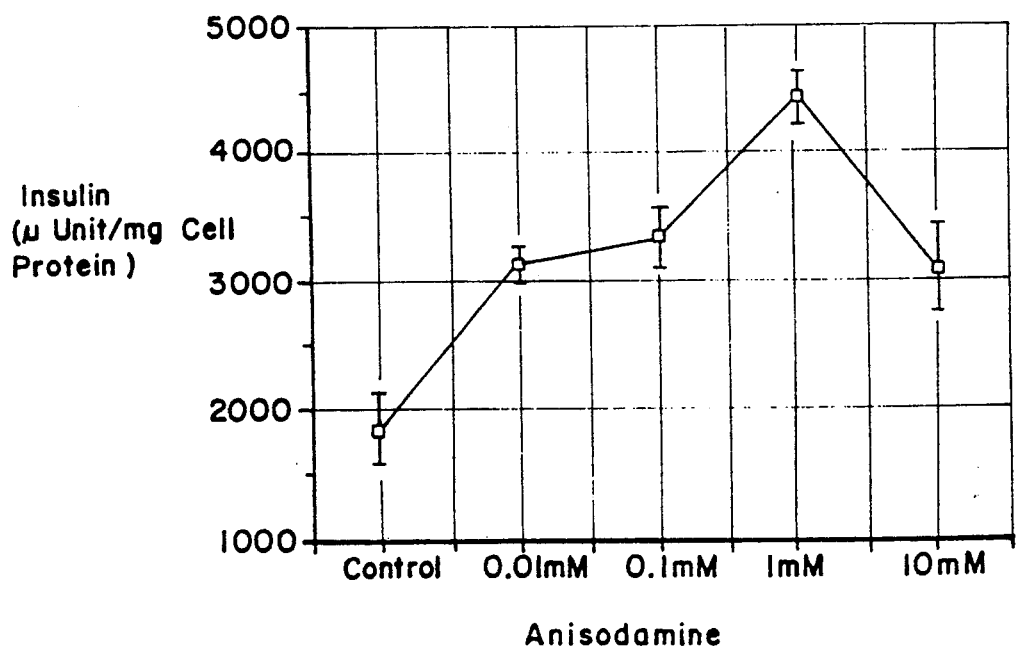
FIG. 4 is a graphic depiction of the effect of anisodamine on insulin secretion.

We found that the presence of anisodamine from 0.01-1 mM, enhanced glucose-induced insulin secretion from β cells in a dose-dependent manner. The results are summarized in FIG. 4. Without knowing why, in vivo studies have demonstrated that administration of anisodamine to diabetics has beneficially reduced the level of hyperglycemia. Y. Z. Zhou, "Investigation of the Effectiveness of Henbane Drug for Treating Diabetes," *The Collection of Reference Material of the* 2nd National Conference for Exchange of Experiences on Research of Microcirculation and Henbane Drugs, 196-198 (1981). In light of our experimental studies, we believe anisodamine can effectively reduce the effects of diabetes by increasing the level of insulin in the body.

2. Alloxan-induced lipid peroxidation

Alloxan-induced lipid peroxidation of isolated β cells and the protection provided by anisodamine were also tested. The experimental system consisted of 0.24 ml of β cell-DPBS suspension, 0.03 ml anisodamine, or DPBS if the system was to be used as a control. To each system 0.03 ml alloxan was added, DPBS if the system was to serve as a control. The final concentration of anisodamine was 1 mg/ml. The final concentration of alloxan was 0.7 mg/ml. Using the method discussed above, the concentration of malondialdehyde was measured after a thirty-minute incubation period.

Figure 5:
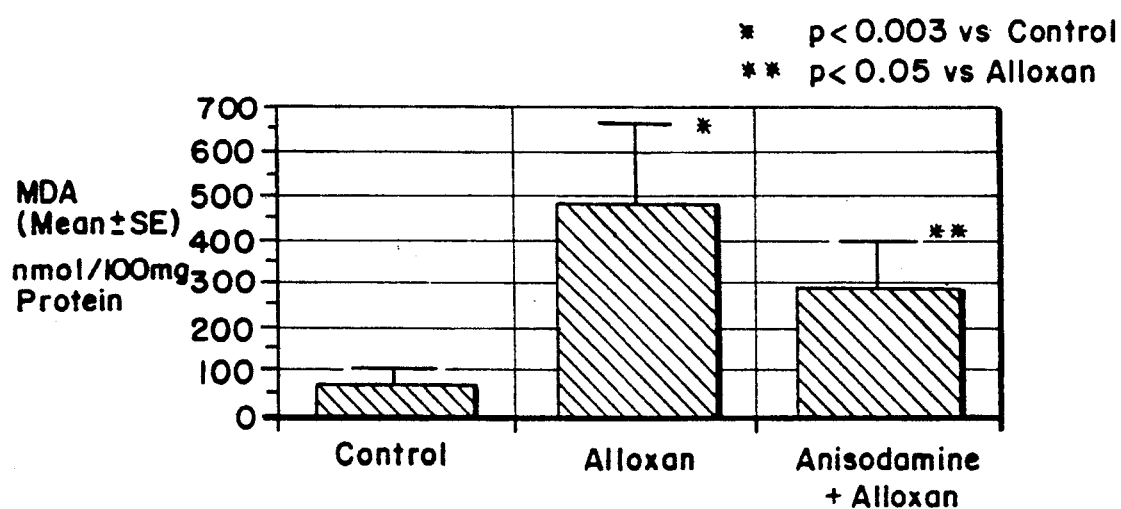
FIG. 5 is a graphic depiction of the effect of anisodamine on the effect of alloxan on malondialdehyde production by $\beta$ cells.

Our studies found that alloxan increaed malondialdehyde production by the β cell by approximately sevenfold (see FIG. 5). However, anisodamine was found again to tremendously attenuate the increase in β cell malondialdehyde production. FIG. 5 shows a 40% attenuation.

All of these examples demonstrate that the beneficial properties of anisodamine administered in effective amounts can be exploited to prevent and relieve pathologic changes associated with the onset and progression of retinopathy or macular degeneration.

The invention has been described with reference to various specific and preferred embodiments and techniques. However, it should be understood that many variations and modifications may be made while remaining within the spirit and scope of the invention.

What is claimed is:

1. A method for protecting the eye against senile macular degeneration comprising administering anisodamine or a pharmaceutically-acceptable salt thereof to the eye of a human in need thereof in an amount effective to protect the eye against senile macular degeneration.

2. The method of claim 1 wherein anisodamine or the pharmaceutically-acceptable salt thereof is parenterally administered in association with a pharmaceutically-acceptable liquid carrier.

3. The method of claim 1 wherein the effective amount administered is about 0.5-50 mg per kilogram body weight, per day.

4. The method of claim 1 wherein anisodamine is topically administered.

5. The method of claim 1 wherein anisodamine is administered in the form of eyedrops.

* * * * *